United States Patent [19]

Neal

[11] 3,944,625

[45] Mar. 16, 1976

[54] SEPARATION OF MANNITOL FROM GALACTITOL

[75] Inventor: John A. Neal, Bellingham, Wash.

[73] Assignee: Georgia-Pacific Corporation, Portland, Oreg.

[22] Filed: Apr. 17, 1975

[21] Appl. No.: 569,079

Related U.S. Application Data

[63] Continuation-in-part of Ser. No. 328,966, Feb. 2, 1973, abandoned.

[52] U.S. Cl. ....... 260/637 R; 260/439 R; 260/635 C
[51] Int. Cl.² .......................................... C07C 29/24
[58] Field of Search ...................... 260/637 R, 635 C

[56] References Cited
UNITED STATES PATENTS

| | | | |
|---|---|---|---|
| 2,917,390 | 12/1959 | Apel et al. | 260/635 C |
| 2,989,569 | 6/1961 | Apel | 260/635 C |
| 3,227,707 | 1/1966 | Langer | 260/637 R |

FOREIGN PATENTS OR APPLICATIONS

| | | | |
|---|---|---|---|
| 645,019 | 7/1962 | Canada | 260/635 C |
| 941,797 | 11/1963 | United Kingdom | 260/635 C |
| 727,677 | 5/1955 | United Kingdom | 260/637 R |

OTHER PUBLICATIONS

Lange, "Handbook of Chemistry", 10th ed. (1961), pp. 804, 805.

*Primary Examiner*—Joseph E. Evans
*Attorney, Agent, or Firm*—Peter P. Chevis

[57] ABSTRACT

A process for the separation of mannitol from galactitol is disclosed which comprises selectively crystallizing mannitol from an alkanol-water solution of the mixture to which a small amount of a soluble salt of an iron, nickel, or cobalt has been added.

16 Claims, No Drawings

SEPARATION OF MANNITOL FROM GALACTITOL

This is a continuation-in-part of patent application Ser. No. 328,966, filed Feb. 2, 1973 now abandoned.

This invention pertains to the separation of hexitols or sugar alcohols. More particularly it pertains to the separation of mannitol from galactitol.

While mannitol is presently principally used in pharmaceutical applications, serving as a base in multi-layer and press-coated tablets of vitamins, antacids, aspirin and other pharmaceuticals, it is an old, well-known alcohol and continues to find use in synthetic resins, fluxes, antioxidants and other uses. Its properties are especially effective for tablet-coating, since it provides a sweet taste and masks the unpleasant taste of many of the drugs used in the tablet. Its low affinity for water is also desirable resulting in the tablet maintaining a low moisture content.

Substantial quantities of mannitol are prepared by hydrogenation of sugars recovered from natural sources. Large quantities of mannose are available in pulping liquors resulting from pulping of wood in the production of pulp or cellulose. The pulping liquors, for example spent sulfite liquor solids from pulping softwoods, contain up to about 20% hexoses of which about one half is mannose. Also, in the hydrolysis of lignocellulosic material or in the prehydrolysis stage in pulping operations, the extracts obtained are substantially wood sugars, predominately mannose. While these liquors contain mannose, the mannose is present in a complex mixture with other wood sugars and when recovered from these mixtures contains substantial amounts of galactose or galactitol, if the mixture is hydrogenated to convert the mannose to mannitol prior to recovery. Likewise polysaccharides such as galactomannans are recovered by known processes from numerous plants which upon hydrolysis yield mixtures of galactose and mannose with mannose predominating. Mannitol also occurs in plants and when recovered is also in a complex mixture with sugars and other sugar alcohols. Many of the sugars and sugar alcohols have sufficiently different characteristics to permit relatively easy separation. However, the characteristics of mannose and galactose as well as mannitol and galactitol are such that the normal known methods of liquid extraction or crystallization often used in sugar or sugar alcohol separations are not applicable. Detailed description of the methods commonly used are found in numerous patents and texts on carbohydrate chemistry, such as for example "Methods in Carbohydrate Chemistry", by R. L. Whistler et al., Editors, Volumes 1 to 6 and the text "The Carbohydrates", edited by W. Pigman and D. Horton both published by Academic Press Inc., New york, New York and others including various college organic chemistry texts. While the presence of galactitol may not be detrimental for some of the uses of mannitol, its presence in even a relatively small amount is generally undesirable.

It is, therefore, an object of this invention to provide a process for the separation and recovery of mannitol from a mannitol-galactitol mixture. A further object is to provide a process for purification of mannitol. A still further object is to provide a process for the recovery of mannitol from mixtures obtained by reduction of wood sugars obtained in prehydrolysis liquors and spent sulfite liquors in wood-pulping operations.

The above and other objects are attained according to this invention by crystallizing mannitol from an alkanol-water or dioxane-water solution containing the mannitol and galactitol. Prior to crystallization, ferric, nickel or cobalt ions are added to the solution in an amount sufficient to complex with the galactitol. By the addition of ferric or the nickelous or cobaltous ions to the solution, it is believed that these ions complex selectively with the galactitol which complex remains soluble permitting the mannitol to crystallize out in a relatively pure state. Both mannitol and galactitol are soluble in water and have limited solubility in the lower alkanols and dioxane with mannitol being somewhat more soluble in both water and the alkanols.

While the process may be used for fractionation and recovery of mannitol from any mixtures of sugar alcohols, containing galactitol generally the normal procedures are less costly and sufficiently effective to obtain crude mannitol fractions. These fractions contain mainly mannitol with the impurities being present in minor proportions with galactitol being the main impurity. Thus, generally the normal procedure used for fractionation and recovery of sugars and/or sugar alcohols are used for obtaining crude fractions of mannitol containing generally 80% mannitol or more of mannitol and the process of this invention then used for further purification of the mannitol.

A convenient method for carrying out the crystallization is to dissolve the mannitol product, containing mainly galactitol and other sugar alcohols and sugars in lesser amounts as impurities, in hot water until a concentrated solution is obtained. To the hot aqueous solution, the metal ion and alkanol are added. The addition of the alkanol decreases the solubility of the sugar alcohols in the solution enhancing the crystallization and increasing the yield of the mannitol. It is not necessary to dissolve the mannitol product to be purified in the water prior to addition of the alkanol. The product may be dissolved in a heated alkanol-water solution and the metal ion added before or after dissolving the mannitol product in the solution. Similar procedures may be followed when dioxane is used in place of alkanol. Also, the various processes and equipment commonly used in crystallization operations may be used for the crystallization of the mannitol. The crystallization can be effected just by cooking or evaporating the solution or a combination of both. The mother liquor or the solution after the crystallization of the mannitol may be distilled to recover the alkanol for reuse, or it may be recycled directly with a sufficient proportion of mother liquor being replaced by fresh solution to keep the concentration of galactitol and other impurities at acceptable levels. Generally the mannitol crystallized from mixtures of mannitol and galactitol obtained from spent sulfite liquor sugar fractions is of sufficient purity that it may be used in many applications without further purification or recrystallization. This is especially true if ferric ions are used as the complexing metal. When nickel or cobalt are used, further crystallization and purification may be necessary to remove the trace amounts of the metal which may be present due to the toxic nature of the metal if the product is to be used for pharmaceutical purposes. Also when the process is used on mixtures containing a major portion of galactitol with the mannitol being present only in minor portions, the product obtained would contain a higher content of galactitol upon the first crystallization and further recrystallizations may be required to obtain mannitol in purified form.

While 1,3- or 1,4-dioxane or any alkanol having from 1 to 4 carbon atoms or mixtures thereof can be used for the solution for the crystallization, methanol or ethanol or a mixture of one of the other alkanols with ethanol or methanol is preferred. The removal of these alkanols from the crystallized mannitol is simplified by the lower boiling point of methanol and ethanol. The amount of alkanol or dioxane used in the solution may be widely varied from as low as 1 or 2 volume percent to the alkanol or dioxane being the major constituent of the solvent. For convenience, the content is usually increased at least to 25 or 30 percent. Solutions containing from 60 to 90 percent or higher of methanol, ethanol, or dioxane are preferred. With the higher alkanols, the amount of the alkanol added may be somewhat decreased over the amount of methanol or ethanol used, due to the decreased solubility of the sugar alcohols in the high alkanols. Generally the amount of alkanol or dioxane added is adjusted to obtain practical yields under the conditions of the crystallization. For example, from 2 to 10 grams of mannitol per hundred milliliters of solution may be crystallized out just upon cooling hot solutions under atmospheric conditions to room temperature. The yields can be further increased without evaporation by cooling to a lower temperature, such as 0°C or lower.

Galactitol is somewhat less soluble than mannitol in both water and the lower alcohols but is maintained in solution by the addition of the particular metal ion. Sufficient amount of the metal ion is added to complex with the galactitol to keep the galactitol from crystallizing. The amount of metal added may be widely varied, since more than one complex may be obtained. However, the minimum amount required is easily determined by routine crystallization, with various amounts of the metal being added. Generally, from about 0.8 to 1.5 mole of the metal per mole of galactitol present is used. Smaller amounts, for example, as low as 0.1 mole per mole of galactitol may be effective in hindering the crystallization of the galactitol; however, generally larger amounts are desirable in the event that the mixture being purified may contain sugars or other sugar alcohols which may also complex or react with the metal. The amount of the metal may also be increased so that the metal content may be present in the ratio of 2 to 3 moles per mole of galactitol. However, using the high levels of the metal results in larger amounts of the metal being carried down with the mannitol by adherence or occlusion of the mother liquor to the mannitol crystals.

The metal ions are generally added to the solution as soluble iron, nickel or cobalt compounds having sufficient solubility in the alkanol-water solution to provide the desired metal concentration in solution. Both ferric and ferrous iron salts and compounds may be used, since in the amount of the metal added, ferrous ions are oxidized in the solution to the ferric state in a relatively short time under normal conditions. The metals may also be introduced into the solution by addition of compounds which are weak complexes of the metal or any other compound which ionizes in the solution to provide the required metal ions. Illustrative examples of the metal compounds such as salts and complexes which are soluble in alkanol-water solutions in an amount to provide the desired concentration of the metal ions for complexing are: iron chloride, iron hydrosulfite, iron nitrate, iron fluoride, iron acetate, iron maleate, iron oleate, nickelous chloride, nickelous nitrate, nickelous acetate, and cobaltous chloride, nitrate, or acetate, and other soluble organic or inorganic compounds.

EXAMPLE I

A mixture of mannitol and galactitol was obtained from the reduction of wood sugars recovered from a calcium base spent sulfite liquor. The sugar fraction was recovered from the calcium base liquor by alcohol extraction using the method described by L. A. Boggs in a paper presented at the 155th ACS National Meeting in 1968 at San Francisco, California. The description of the process is given in the "Abstract of Papers" of the meeting published by the American Chemical Society in 1968. The spent sulfite liquor was contacted with a methanol-water solvent containing 95% methanol resulting in the major portion of the lignosulfonates being insoluble with the low-molecular weight materials and the sugar being extracted. The methanol was distilled from the solvent fraction and the solvent changed to water. The resulting solution was then filtered to remove the insolubles and deionized by successively passing the filtrate through a strong cation exchange resin in an acid form to remove the cation and a weak anion exchange resin in the free-base form to remove the anions. The effluent obtained was concentrated under reduced pressures to give a heavy syrup containing mainly the sugars.

The sugar fraction was then reduced to the sugar alcohols by hydrogenation with Raney nickel catalyst at a temperature of about 100°C and an initial pressure of around 1,500 pounds per square inch. The sugar alcohols obtained were dissolved in methanol and crystallized by cooling to obtain a mannitol fraction which contained approximately 5% galactitol as the main impurity.

The above product in an amount of 18.2 grams was dissolved in 100 milliliters of water at approximately 60°C, and 300 milliliters of methanol at 50°C were added slowly to the warm aqueous solution. To the resulting solution, an additional 100 milliliters of warm methanol containing 2.7 grams of ferric chloride hexahydrate was added. The solution was cooled slowly to 15°C resulting in mannitol crystallizing out. The mannitol crystals formed were collected and washed with 100 milliliters of methanol. The first crop of crystals obtained was in an amount of 12.1 grams. The wash methanol was combined with the mother liquor and the mixture was then evaporated to a final volume of 15 milliliters after which 75 milliliters of warm methanol were added to the remaining warm solution. After cooling to 15°C, a second crop of mannitol crystals was obtained which after washing was in an amount of 4.6 grams.

The mannitol recovered had a melting point in the range of 163° to 166°C as compared to 156° to 159°C for the mannitol fraction prior to the crystallization in the presence of ferric ions. An infrared spectrum made of the recovered mannitol indicated the absence of the strong galactitol absorption bands at 8.95, 9.55, and 10.80 microns, and gave a spectrum substantially identical in the range of 2 to 16 microns to that of a reagent grade commercially available mannitol.

The iron content of the mannitol obtained upon crystallization, as described above, was 0.0015 percent. The iron content in other runs was reduced to as low as 0.0009 percent by adding crystals to warm methanol and mixing the suspension for about 1 hour to wash the crystals.

A sample of the mannitol fraction was also recrystallized without the addition of the iron. The sample in an amount of 1.8 grams was dissolved in 50 ml of a methanol-water solution containing 75% methanol. The methanol-water solution was at about 60°C when the sample was dissolved, and upon cooling crystallization was obtained. An infrared spectrum of the crystallized product contained the strong galactitol absorption bands at 8.95, 9.55 and 10.80 microns at about the same relative intensity as that of the mannitol fraction prior to the recrystallization.

EXAMPLE II

An aqueous solution of mannitol and galactitol was prepared by dissolving 4 grams of mannitol and 1 gram of galactitol in 30 milliliters of warm water. To the warm solution, 40 milliliters of 95 percent ethanol at 65°C and an additional 40 milliliters of the ethanol containing 0.25 gram of dissolved ferric chloride hexahydrate was added. Mannitol was crystallized from the solution by slowly cooling the solution to room temperature and maintaining it at room temperature overnight. The crystals of mannitol were recovered from the mother liquor by filtration and were washed with warm 95 percent ethanol. The product recovered was in an amount of 1.7 grams of mannitol having an infrared spectrum substantially the same as that of reagent grade mannitol free of the strong absorption bands associated with galactitol.

EXAMPLE III

A mixture of mannitol and galactitol containing about 8.5 grams of mannitol and 0.45 gram of galactitol was dissolved in 50 milliliters of water. Methanol at 50°C was added to obtain a total volume of 150 milliliters. To this solution, a solution of 50 milliliters of methanol containing 1.2 grams of nickel chloride hexahydrate was added. The solution was slowly cooled to ambient room temperature, maintained at room temperature overnight, and then cooled to 4°C for 4 hours. Seven grams of crystals were obtained.

The infrared spectrum indicated that only a trace of galactitol was present. The product had a melting point in the range of 163°C to 166°C.

EXAMPLE IV

A mixture of mannitol and galactitol as described in Example I above was purified by crystallizing the mannitol from the mixture in a dioxane-water solution in presence of ferric ions. The mixture of mannitol and galactitol in an amount of 3 grams was dissolved in 16 milliliters of warm water, after which 20 milliliters of warm 1,4-dioxane were added. To this mixture, an additional 30 milliliters of warm dioxane was added in which 0.5 gram of ferric chloride hexahydrate had been dissolved. The mixture was cooled to 4°C and maintained at that temperature overnight. The crystals were recovered by filtration, washed with methanol and after drying weighed. The 1.0 gram of product obtained in the one-stage crystallization was substantially pure mannitol having an infrared spectrum similar to that of the product obtained in Example I.

What is claimed is:

1. A process for the recovery of mannitol from a mixture containing predominately mannitol and galactitol which comprises crystallizing the mannitol from a solution of the mixture in an alkanol-water or a dioxane-water solution containing at least 1 volume percent of the alkanol or dioxane, said solution of the mixture containing ferric, nickelous, or cobaltous ions in an amount sufficient to complex with the galactitol, said alkanol having from 1 to 4 carbon atoms.

2. A process according to claim 1 wherein the solution contains nickel ions.

3. A process according to claim 1 wherein the solution contains ferric ions in an amount of from 0.1 to 3 mole per mole of galactitol in solution.

4. A process according to claim 3 wherein the solution is an ethanol-water solution and the ferric ions are added to the solution by addition of an iron salt.

5. A process according to claim 3 wherein the solution is a methanol-water solution and the ferric ions are added to the solution by addition of an iron salt.

6. A process according to claim 3 wherein the solution is a dioxane-water solution and the ferric ions are added to the solution by addition of an iron salt.

7. A process according to claim 4 wherein the iron salt is ferric chloride.

8. A process according to claim 5 wherein the iron salt is ferric chloride.

9. A process according to claim 6 wherein the iron salt is ferric chloride.

10. A process for the recovery of mannitol from a mixture of mannitol and galactitol containing predominantly mannitol which comprises dissolving the mixture in water at an elevated temperature, intermixing an alkanol having from 1 to 4 carbon atoms or dioxane with the aqueous solution in an amount of at least 1 volume percent, adding a metal compound to obtain ferric, nickelous, or cobaltous ions in the solution in an amount sufficient to complex with the galactitol, and crystallizing the mannitol from the resulting solution.

11. A process according to claim 10 wherein the metal ions are ferric ions added as an iron salt in an amount of from 0.8 to 1.5 mole of the metal ions per mole of galactitol in solution.

12. A process according to claim 11 wherein the mannitol-galactitol mixture is obtained by reduction of a fraction of sugars obtained by hydrolysis of wood.

13. A process according to claim 12 wherein the sugar fraction is obtained by fractionation of a spent sulfite liquor.

14. A process according to claim 13 wherein the mannitol-galactitol mixture is dissolved in the water to obtain a substantially saturated solution at a temperature of from 80° to 90°C with which methanol is intermixed to obtain a solution containing from 60 to 90% methanol and the remainder water, and the mannitol is crystallized out by cooling the methanol containing solution to a temperature of from 0° to 30°C.

15. A process according to claim 13 wherein the mannitol-galactitol mixture is dissolved in water to obtain a substantially saturated solution at a temperature of from 80° to 90°C with which ethanol is intermixed to obtain a solution containing from 60 to 90% ethanol and the remainder water, and the mannitol is crystallized out by cooling the ethanol containing solution to a temperature of from 0° to 30°C.

16. A process according to claim 13 wherein the mannitol-galactotol mixture is dissolved in water to obtain a substantially saturated solution at a temperature of from 80° to 90°C with which dioxane is intermixed to obtain a solution containing from 60 to 90% dioxane and the remainder water, and the mannitol is crystallized out by cooling the dioxane containing solution to a temperature of from 0° to 30°C.

* * * * *